United States Patent [19]

Itoh

[11] Patent Number: 4,757,820
[45] Date of Patent: Jul. 19, 1988

[54] ULTRASOUND THERAPY SYSTEM

[75] Inventor: Ayao Itoh, Yokohama, Japan

[73] Assignee: Kabushiki Kaisha Toshiba, Kawasaki, Japan

[21] Appl. No.: 838,953

[22] Filed: Mar. 12, 1986

[30] Foreign Application Priority Data

Mar. 15, 1985 [JP] Japan .................................. 60-51717

[51] Int. Cl.$^4$ ............................................. A61B 10/00
[52] U.S. Cl. .................................. 128/660; 128/24 A
[58] Field of Search ............. 128/328, 29 A, 660–663, 128/305, 804

[56] References Cited

U.S. PATENT DOCUMENTS

| | | | |
|---|---|---|---|
| 3,051,167 | 8/1962 | Fry | 128/24 A |
| 3,237,623 | 1/1966 | Gordon | 128/24 A |
| 3,958,559 | 5/1976 | Glenn et al. | 128/660 |
| 4,240,295 | 12/1980 | Uranishi | 128/660 X |
| 4,246,784 | 1/1979 | Bowen | 73/339 A |
| 4,292,977 | 10/1981 | Krause et al. | 128/660 X |
| 4,315,514 | 2/1982 | Drewes et al. | 128/24 A X |
| 4,390,025 | 6/1983 | Takemura et al. | 128/660 |
| 4,484,569 | 11/1984 | Driller et al. | 128/660 |
| 4,526,168 | 7/1985 | Hassler et al. | 128/24 A X |
| 4,586,512 | 5/1986 | Do-huu et al. | 128/660 |
| 4,617,931 | 10/1986 | Dory | 128/328 |
| 4,620,545 | 11/1986 | Shene et al. | 128/24 A X |
| 4,620,546 | 11/1986 | Aida et al. | 128/660 |

FOREIGN PATENT DOCUMENTS

| | | | |
|---|---|---|---|
| 0068961 | 1/1983 | European Pat. Off. | 128/24 A |
| 3119295 | 12/1982 | Fed. Rep. of Germany | 128/24 A |

OTHER PUBLICATIONS

Forssmann, B. et al., Device for Locating and Positioning for Concrement Disruption; Europäische Patentanmeldung, 0168559, publ. Apr. 17, 1985.
Local Hyperthermia Induced by Focussed and Overlapping Ultrasonic Fields: K. Hynynen, et al., Ultrasound in Med & Biol., vol. 9, No. 6, p. 621, 1984.
Experience with a Multitransducer Ultrasound System for Localized Hyperthermia of Deep Tissues; P. Fessenden, et al., IEEE Transactions on Biomedical Engineering, vol. BME 30, No. 126, 1984.
Annular Array Transducer for Deep Acoustic Hyperthermia: J. P. Do–Huu, et al., 1981 Ultrasound Symposium, p. 705.
IEEE Transactions on Biomedical Engineering, vol. BME-31, No. 1, Jan. 1984, pp. 136–149, IEEE, New York, U.S.; J. W. Strohbehn et al.: "A Survey of Computer Simulations of Hyperthermia Treatments".

Primary Examiner—Francis J. Jaworski
Attorney, Agent, or Firm—Oblon, Fisher, Spivak, McClelland & Maier

[57] ABSTRACT

An ultrasound therapy system comprises an annular array ultrasound transducer, a mechanical driver, a transmitter/receiver, and a controller. The controller includes an imaging controller, a heating controller, and a select controller. The mechanical driver mechanically drives the transducer to change at least one of the position and direction of ultrasound beams transmitted and received by the transducer. The transmitter/receiver may supply drive signals to the respective elements of the transducer, and receive the ultrasound echo signals from the elements. The imaging controller gives a first drive command to the transmitter/receiver, and at the same time drives the mechanical driver, radiates scanning ultrasound beams for tomographing through the transducer, and obtains a tomogram of a target portion in a patient from the echo signal derived from the transmitter/receiver. The heating controller drives the transmitter/receiver by a second drive signal to cause the transducer to radiate heating ultrasound beams. The heating ultrasound beams heat the target. These imaging and heating controllers are selectively activated by the select controller.

4 Claims, 4 Drawing Sheets

ULTRASOUND THERAPY SYSTEM

BACKGROUND OF THE INVENTION

The present invention relates to an ultrasound therapy system which obtains a tomogram of biological tissue and effects the treatment of an affected part.

Recently, various therapy systems using ultrasound, have been developed. On example is hyperthermia treatment, which is one method of treating malignant neoplasm, generally called cancer. Tumors are more sensitive to temperature than healthy tissue. Tumorous tissue dies or does not propagate if it is subjected to a temperature of 42.5° C. or more. The treatment based on this phenomenon is called the hyperthermia treatment. Many clinical examples have shown that hyperthermia treatment effectively restricts the growth of various types of tumorous tissue and even reduces tumorous tissue.

Many types of hyperthermia treatment are known. Of these methods, local hyperthermia treatment is particularly effective.

Local hyperthermia treatment using electromagnetic waves such as microwaves has been proposed and put into practice. This method, however, has one major disadvantage. That is, it is very difficult to accurately heat deep tumors. This is due to the attenuating characteristic of electromagnetic waves having wave lengths suitable for the hyperthermia treatment. (This characteristic depends on the electromagnetic wave length.) In this treatment, examples of effective hyperthermia treatment are limited to surfacial tumors located within about 5 centimeters of the epidermis.

To solve this problem, another method of hyperthermia treatment has been studied and proposed. This method features ultrasonic waves instead of electromagnetic waves. This is because ultrasonic waves can cause vibration.

Ultrasonic waves are also used to treat calculi such as renal calculi or urinary calculi. In this treatment, high ultrasound beams can be focused on a calculus and effect spallation.

Such ultrasonic treatment requires one of two types of ultrasound transducers. One type of transducer includes a plurality of ultrasound transducer elements 1 each having a concave spherical ultrasound radiation surface, which are arrayed on a concave spherical surface, as shown in FIGS. 1A and 1B. The second type of transducer is annularly arrayed such that a plurality of ring shaped transducer elements 2 are concentrically arrayed as shown in FIGS. 2A and 2B. Both types of transducers focus ultrasound waves on a deep target portion P to effect treatment.

The second type of transducer, i.e. an annular array ultrasound transducer, has especially attractive advantages. With this type of transducer, ultrasound beams can be accurately focused on a deep target, and the distance from the transducer to the point of focus can be electrically varied.

In a conventional system of this type, recognition of the position and configuration of the target to be treated is executed by a diagnostic apparatus for checking and diagnosing a state and location of specific tissue in a patient. To treat a tumor, however, another apparatus is required. As a result of using different apparatuses, healthy tissue is frequently treated. Naturally, this is undesirable. In this respect, this method does not permit utilization of the high capacity to focus ultrasound beams, which prevents maximum treatment of diseased tissue. The need for two types of apparatuses also makes treatment complicated and cumbersome. One example is positioning the ultrasonic transducer.

SUMMARY OF THE INVENTION

Accordingly, an object of the present invention is to provide an ultrasound therapy system which can locally and selectively treat only a target portion in a patient by accurately locating it and recognizing a configuration of it, with an easy operation and good operability.

To achieve the above object, an ultrasound therapy system comprises an annular array ultrasound transducer having a plurality of ring transducer elements concentrically arrayed, a tomographing processor for driving the transducer by a first drive signal to transmit ultrasonic waves and receiving ultrasound echo waves reflected from internal tissues of a patient, to thereby provide a tomogram of the internal tissues, a treating controller for driving the transducer by a second drive signal to transmit ultrasonic waves for treatment purposes, and a selector for selectively driving the tomographing processor and the treating controller.

In this system, one annular array ultrasound transducer is used for transmitting and receiving ultrasound to obtain tomograms as well as for transmitting ultrasound for treatment.

According to this invention, a single ultrasound transducer tomographs a target for observing the target and positioning it, and treats the target only. With this feature, exact positioning and treating the target are secured to provide an effective treatment.

In the conventional system of this type, two different apparatuses must be used, one for detecting the tomogram information and the other for treating the specific portion in a patient. Therefore, the transducers of both the apparatuses must be positioned so that ultrasound beams are radiated toward the target portion. The positioning requires some skill for operators.

This problem was successfully solved by the ultrasound system according to this invention, which uses a single ultrasound transducer. Further, space for system installation is saved and cost to manufacture the system is reduced.

In the ultrasound therapy system, the treating operation is not performed during the tomographing operation. One might consider that this fact is disadvantageous for diagnosis and treatment work. In practical use, however, there is no need for real time tomographing. The tomographing is only needed when, after positioning and orientation of the transducer, and drive conditions of the transducer are set up while observing the displayed tomogram, other conditions than those as set change.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENT

Figure 3:
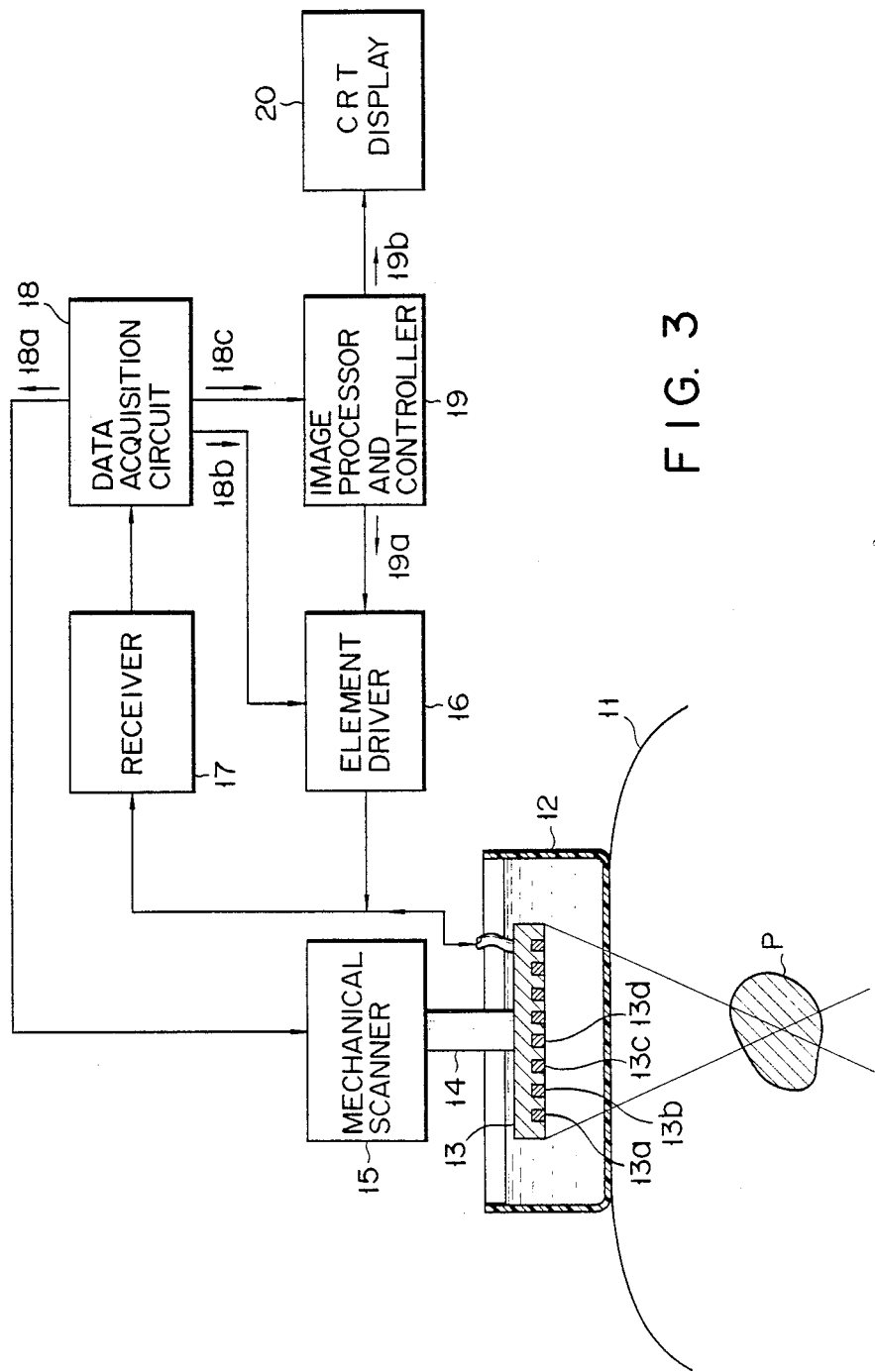
FIG. 3 is a block diagram illustrating an arrangement of an ultrasound system for hyperthermia treatment to which the present invention is applied.
Figure 4:
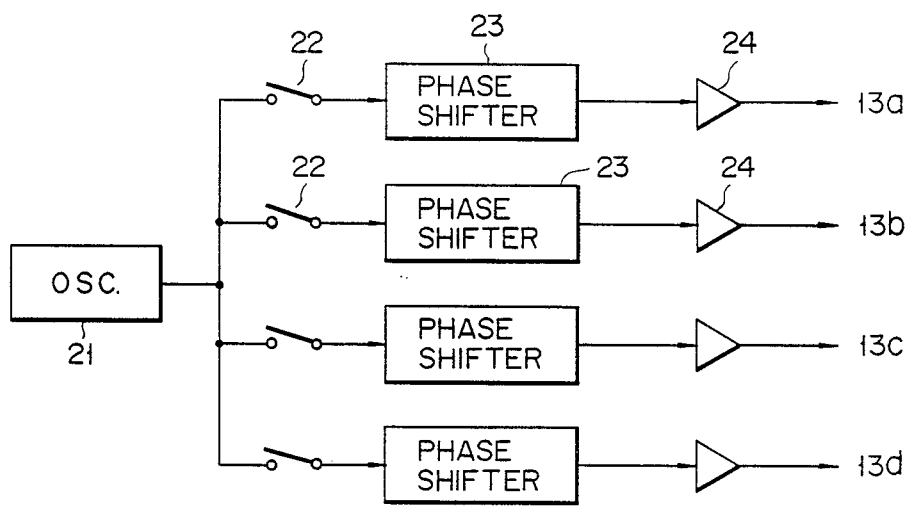
FIG. 4 is a block diagram illustrating a circuit arrangement of an element driver used in the circuit shown in FIG. 3.

As shown in FIG. 3, an ultrasound system for hyperthermia treatment according to the present invention is comprised of annular array ultrasound transducer 13, rod 14, mechanical scanner 15, transducer element driver 16, receiver 17, data acquisition circuit 18, image processor/controller 19, and CRT (cathode ray tube) display 20.

Figure 1A:
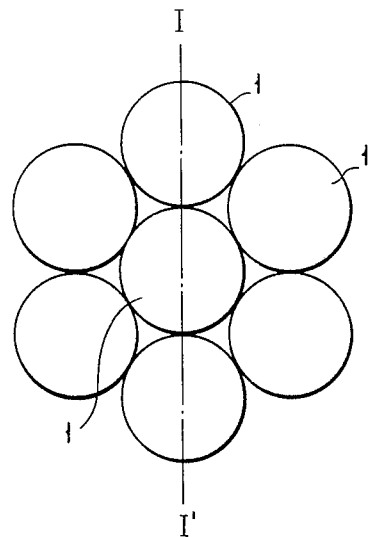
FIGS. 1A and 1B are plan and cross sectional views of a conventional ultrasound transducer using spherical transducer elements in use for hyperthermia treatment, the plan view illustrating an array of spherical transducer elements and the cross sectional view taken on line I—I in FIG. 1A well illustrating the transducer elements in relation with transmitted ultrasound beams.
Figure 1B:
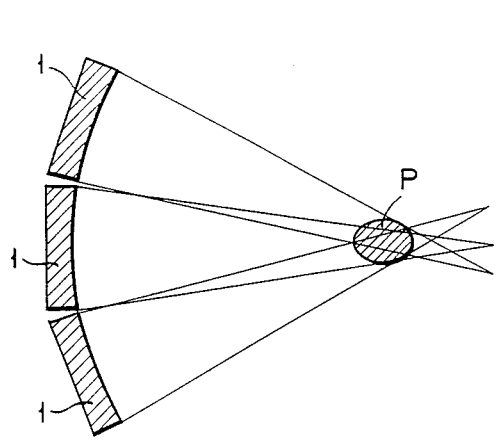
Figure 2A:
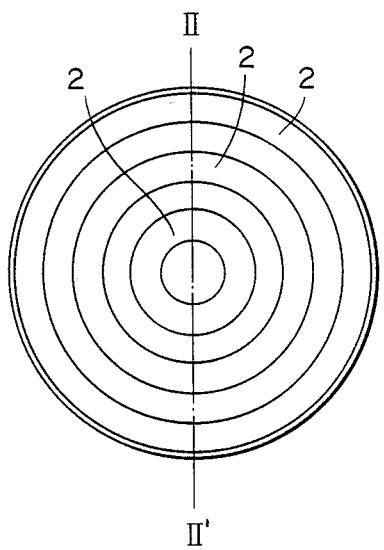
FIGS. 2A and 2B show plan and cross sectional views of another conventional ultrasound transducer using annular array ultrasound transducer elements in use for ultrasound hyperthermia treatment, the plan view illustrating an array of the transducer elements, and the cross sectional view taken on line II—II in FIG. 2A well illustrating the elements with relation to radiated ultrasound beams.
Figure 2B:
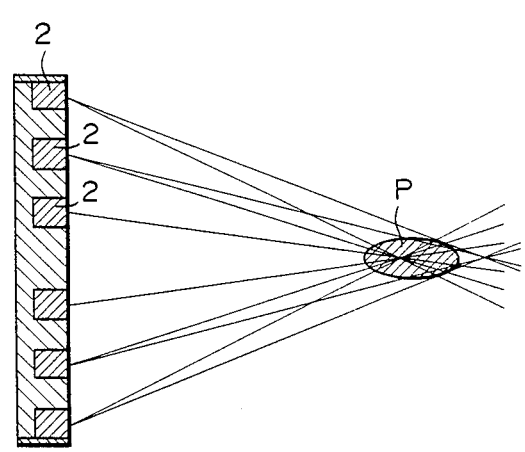

Transducer 13, like the ultrasound transducer shown in FIGS. 2a and 2B, comprises a plurality of ring transducer elements 13a to 13d concentrically arrayed. Water bag 12, i.e. a bag containing water, is placed on patient 11 in contact with his skin. Annular array ultrasound transducer 13 is disposed in the water in bag 12. Transducer 13 is coupled with mechanical driver 15 by means of rod 14. For tomographing, the driver 15 mechanically drives transducer 13 in a scanning manner.

Transducer elements 13a to 13d of transducer 13 are driven by the drive signal derived from driver 16, and project ultrasound beams into the inside of patient 11.

Element driver 16 is comprised of oscillator 21, a plurality of switches 22, a plurality of phase shifters 23, and a plurality of drive amplifiers 24. Oscillator 21, serving as a signal source, is connected through switches 22 respectively to the plurality of phase shifters 23. Each of these phase shifters 23 delays a signal from oscillator 21 to phase shift the signal. These phase shifters 23 are coupled with drive amplifiers 24 of a variable gain for amplifying the signals from the phase shifters. The output signals from amplifiers 24 drive elements 13a to 13d.

Echoes of ultrasonic waves coming from the inside of patient 11 are received by receiver 17 through transducer 13. The echo signals output from receiver 17 when it receives echo waves are input to data acquisition circuit 18. Circuit 18 supplies control signal 18a to scanner 15. Circuit 18 further supplies to driver 16 control signal 18b containing transducer element drive conditions for tomographic imaging. Data acquisition circuit 18 additionally supplies imaging signal 18c for imaging a C-mode image to image processor/controller 19. Image processor/controller 19 applies to driver 16 control signal 19a containing element drive conditions for heating, and further applies to CRT display 20 signal 19b for realizing the three dimensional display or C mode image display. Display image signal 19b is produced by image processor/controller 19 using the signal 18c, derived from circuit 18, to form the C-mode image. In a C-mode imaging, only the components of the ultrasound echo signals reflected at a specific depth of an object to be investigated, i.e. the internal tissue of patient 11, are collected and arranged according to the locations as reflecting the echo waves, and displayed with varied graduation to give a two dimensional image (C-mode image).

In this example, the combination of scanner 15, driver 16, receiver 17, data acquisition circuit 18, and image processor/controller 19 takes a tomogram and performs the image formation. The combination of image processor/controller 19 and display 20 visualizes the tomogram. The heating control of this system is performed through the operation of driver 16 in a heating mode, which is controlled by control signal 19a from image processor/controller 19.

The operation of the ultrasound system for hyperthermia treatment as mentioned above will be described in detail referring to FIGS. 5 and 6. The system will operate selectively (if necessary, alternatively) in either of two operation modes. In the first mode, an image (C-mode image or a three dimensional (3D) image based on it) of a tumor location and its periphery is taken and visualized. In the second mode, only the tumor is heated. The ultrasonic wave used in the first mode, or tomogram display mode, is a pulsative wave. The wave in the second mode, or in the heating mode, is a continuous wave.

In the tomographing mode, data acquisition circuit 18 sends control signal 18b to element driver 16. The control signal 18b is used for setting up element drive conditions (the phase shifts of phase shifter 23, i.e. delay time and gain of drive amplifiers 24). The conditions contain the condition to focus the ultrasound beams coming from transducer 13 at the tumor portion, i.e. the tumor P and its periphery, at the depth d from the skin of patient 11. After the element drive conditions are set up, data acquisition circuit 18 supplies control signal 18a to mechanical scanner 15. Scanner 15 responds to control signal 18a to mechanically drive transducer 13 in a scanning manner by rod 14. This scanning operation may be depicted by dotted line in FIG. 5, for example, and is realized by moving the whole transducer 13 in a spiral fashion. In connection with such scanning operation of transducer 13, driver 16 drives the elements 13a to 13d of transducer 13 in a pulsative fashion with predetermined repetition periods under the above element drive conditions. The elements generate ultrasound beams.

The ultrasound beams projected from transducer 13 into the interior of patient 11 are reflected at the tissue in patient 11. The reflected beams, i.e. echo beams, are received by transducer 13 which in turn produces electrical signals representing the received echo beams. The electrical signals are received by receiver 17. Then, the phases of these signals are aligned with one another in driver 16, amplified and detected. Data acquisition circuit 18 extracts only the signal components reflected at the tissue at the depth d from the output signal of receiver 17. Of the echo signals output from receiver 17, only the signal components are gated at the timing representing the depth d for extracting these components.

In this way, the information on the C-mode image C1 of the tumor portion at the depth d are obtained.

Then, the element drive conditions of driver 16 is modified so that the ultrasound beam is focused on the position at the incremented depth d+Δd. The above operation is then repeated to obtain the information of a C-mode image C2.

Subsequently, similar operations will be repeated while the focusing positions of the ultrasound beams are shifted by Δd in successive manner. Finally, the information of C mode images Ci (i=1 to n) in various depths are obtained. The C-mode image signal 18c thus obtained is sent to image processor/control circuit 19. This circuit 19 forms a three dimensional image Q of the tumor portion on the basis of the C-mode image information Ci. This 3D image Q, as formed by a conventional technique, is a called wire frame image (see FIG. 6) depicted by wires extending along the outer surface of the 3D image. The 3D image Q formed by image processor/controller 19 is visually displayed by CRT display 20.

The heating operation by this system follows.

In the heating mode of the system, control signal 19a is supplied from image processor/controller 19 to element driver 16. In response to control signal 19a, driver 16 sets up the element drive conditions for heating tumor P, and drives the transducer elements 13a to 13d of transducer 13 according to the conditions. The drive conditions include phase shift conditions for phase shifter 23 to produce ultrasound beams suitable for the shape of tumor P, or the sizes of target P at various depths, and the condition for selection of driven transducer elements by switches 22. The conditions further contain the condition for the gain of drive amplifiers 24 to obtain the drive power appropriate for the treatment of tumor P. This drive power is selected to be larger than that in the tomographing mode as mentioned previously. In the heating mode, the ultrasonic wave transmitted by transducer 13 is a continuous wave.

In heating tumor target P, ultrasound beams are focused on the position of target P at the depth d, with a pattern dimensionally corresponding to tumor P at the depth d, and this target P is heated for a predetermined period of time. Following the completion of the heating, ultrasound beams are focused on the position of target P at the incremented depth d+Δd, with a pattern substantially coincident with the configuration of tumor target P at this depth. Subsequently, the focus points are incremented by Δd, and the tumor target P is irradiated at the corresponding positions with the ultrasound beams patterned to the configuration corresponding to target P at these positions. In this way, target P is effectively and selectively heated.

During the heating operation, scanner 15 stops its scanning operation, and hence transducer 13 is at a standstill. Alternatively, ultrasound beams may be focused so that they form a small spot at a predetermined depth. (This spot may be larger than that for tomographing). Under this alternate condition, transducer 13 is driven for heating by scanner 15 to heat the intended area at various depths.

As seen from the foregoing description, the ultraasound system for hyperthermia treatment can tomograph and heat a target in a patient by a single annular array ultrasound transducer. Therefore, the hyperthermia treatment may be performed accurately but easily.

It is evident that the present invention is not limited to the above specific embodiment, but may be modified within the scope of this invention.

For example, a plurality of annular array ultrasound transducers, not a single one, may be combined and selectively or concurrently driven for tomographic imaging and heating the target.

Figure 5:
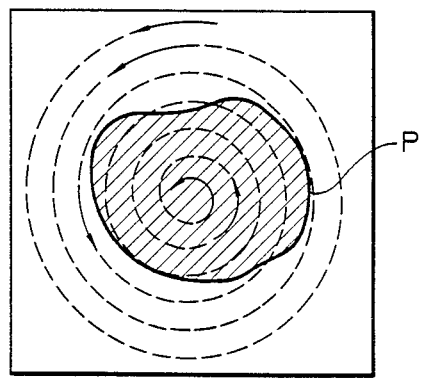
FIG. 5 shows a diagram useful in explaining the scanning by the annular array ultrasound transducer when the system shown in FIG. 3 takes a tomogram.
Figure 6:
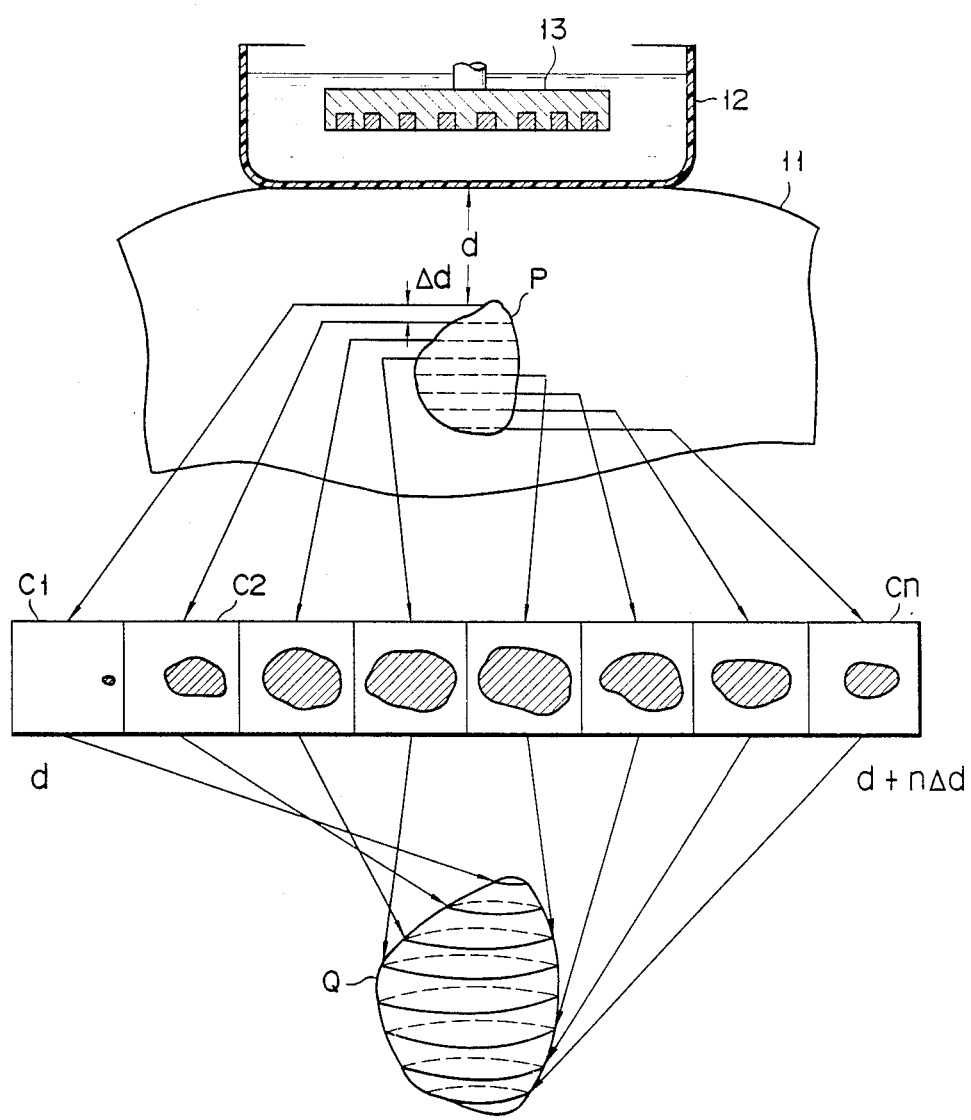
FIG. 6 shows a diagram useful in explaining the operation of the system when it tomographs.

Any other appropriate scanning pattern than that shown in FIG. 5 may be used for forming the C-mode image.

While in the above-mentioned embodiment, the transducer 13 is fixed for scanning with a fixed focus of ultrasound beams, the transducer may be mechanically moved for linear or sector scanning, and with this scanning, the focal point (depth) is varied to obtain a tomogram of a plane containing ultrasound beams, that is, a B-mode image. The use of a combination of C- and B-mode images is also included within the scope of this invention.

In the embodiment as mentioned above, the element drive conditions are automatically set up responsive to the control signal 19a from image processor/controller 19. If necessary, an operator may manually set up the conditions while observing the displayed image by display 20.

Additionally, pulsative ultrasonic waves in place of the continuous wave of ultrasound may be used for treating.

All of the embodiments have been explained with reference to hyperthermia treatment. Needless to say, however, these embodiments can apply to conduct calculus spallation.

Obviously, numerous modifications and variations of the present invention are possible in light of the above teachings. It is therefore to be understood that within the scope of the appended claims, the invention may be practiced otherwise than as specifically described herein.

What is claimed is:

1. An ultrasound therapy system comprising:
an annular array ultrasound transducer having a plurality of ring transducer elements arranged concentrically, for transmitting an ultrasound beam in response to drive signals applied thereto, and for outputting echo signals in response to an ultrasound beam as received;
mechanical drive means for mechanically driving said ultrasound transducer so as to change at least one of position and direction of ultrasound beams transmitted and received by said ultrasound transducer;
transmitting/receiving means for generating and supplying drive signals to said transducer elements to cause said ultrasound transducer to selectively transmit an ultrasound beam for imaging and an ultrasound beam for treatment, and for processing echo signals from said transducer elements corresponding to the received ultrasound beam;
beam pattern control means, connected between said transmitting/receiving means and said ultrasound transducer, comprising means for delaying at least one of the drive signals for driving said transducer elements and the echo signals output from said transducer elements in accordance with a selected one of predetermined delay patterns, thereby controlling a pattern of the ultrasound beam;
imaging means for providing a first drive command to cause said transmitting/receiving means to transmit the imaging ultrasound beam, for driving said beam pattern control means and mechanical drive means so as to scan a patient in three dimensions with the imaging ultrasound beam, and for obtaining and storing three-dimensional image data of the patient from signals generated by said transmitting/receiving means in response to ultrasound echoes from the patient;

treating control means for providing a second drive command to cause said transmitting/receiving means to transmit the treating ultrasound beam, and for causing said ultrasound transducer to transmit the treating ultrasound beam to a target portion of the patient, said heating control means including a means for controlling said beam pattern control means according to the three-dimensional data obtained by said imaging means, such that energy of the treating ultrasound beam is concentrated on the target portion of the patient; and select control means for selectively operating said imaging means and said treating control means.

2. An ultrasound therapy system according to claim 1, in which said treating control means includes a means for controlling said mechanical drive means for driving said ultrasound transducer in relation with the operation of said transmitting/receiving means by said second drive command.

3. An ultrasound therapy system according to claim 1, in which said transmitting/receiving means includes a means for selectively enabling active said transducer elements of said transducer to control the effective diameter of said annular array ultrasound transducer.

4. An ultrasound therapy system according to claim 1, in which said imaging means includes a means for obtaining C-mode image data at various depths in the patient and producing three-dimensional image data from the C-mode image data.

* * * * *